US006558621B1

(12) United States Patent
Banks et al.

(10) Patent No.: US 6,558,621 B1
(45) Date of Patent: May 6, 2003

(54) REMOVAL OF BIOLOGICALLY ACTIVE ORGANIC CONTAMINANTS USING ATOMIC OXYGEN

(75) Inventors: Bruce A. Banks, Olmsted Township, OH (US); Michael A. Banks, Rocky River, OH (US); Eric B. Banks, Westlake, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 75 days.

(21) Appl. No.: 09/606,227

(22) Filed: Jun. 23, 2000

(51) Int. Cl.[7] .............................. A61L 9/00; B08B 3/12; A61F 2/24; A01N 1/00; A61C 8/00
(52) U.S. Cl. ............................ 422/28; 422/32; 422/33; 422/121; 422/292; 422/300; 422/306; 134/1; 134/1.1; 623/920; 435/1; 433/173
(58) Field of Search ................................ 422/1–5, 9–10, 422/20–21, 22–25, 28–37, 107, 119, 121, 123, 292, 294–295, 300, 305, 309, 311, 906, 919; 134/1, 1.1; 623/920; 435/1; 433/173

(56) References Cited

U.S. PATENT DOCUMENTS

| 3,948,601 A |   | 4/1976  | Fraser ............................ 21/54 R |
| 4,566,251 A | * | 1/1986  | Spisak et al. |
| 5,007,232 A | * | 4/1991  | Caudill |
| 5,071,351 A | * | 12/1991 | Green, Jr. et al. ............ 433/173 |
| 5,087,418 A | * | 2/1992  | Jacob ............................ 422/23 |
| 5,163,458 A |   | 11/1992 | Monroe .......................... 134/1 |
| 5,376,400 A | * | 12/1994 | Goldberg et al. ............ 427/2.24 |
| 5,482,684 A |   | 1/1996  | Martens ........................ 422/119 |
| 5,656,238 A |   | 8/1997  | Spencer ......................... 422/23 |
| 5,700,327 A | * | 12/1997 | Babacz et al. ................ 134/1.1 |
| 5,800,542 A | * | 9/1998  | Li .................................. 623/11 |
| 6,238,623 B1 | * | 5/2001 | Amhof et al. ................ 422/58 |

* cited by examiner

Primary Examiner—Robert J. Warden, Sr.
Assistant Examiner—Monzer R. Chorbaji
(74) Attorney, Agent, or Firm—Kent N. Stone

(57) ABSTRACT

Biomedical devices that are to come into contact with living tissue, such as prosthetic and other implants for the human body and the containers used to store and transport them, are together cleaned of non-living, but biologically active organic materials, including endotoxins such as lipopolysaccharides, and assembled into a hermetically sealed package without recontamination. This is achieved by cleaning both the device and package components together in an apparatus, which includes a hermetically sealed chamber, in which they are contacted with atomic oxygen which biocleans them, by oxidizing the biologically active organic materials. The apparatus also includes means for manipulating the device and container and hermetically sealing the cleaned device into the cleaned container to form the package. A calibrated witness coupon visually indicates whether or not the device and container have received enough exposure to the atomic oxygen to have removed the organic materials from their surfaces. Gamma radiation is then used to sterilize the device in the sealed container.

19 Claims, 5 Drawing Sheets

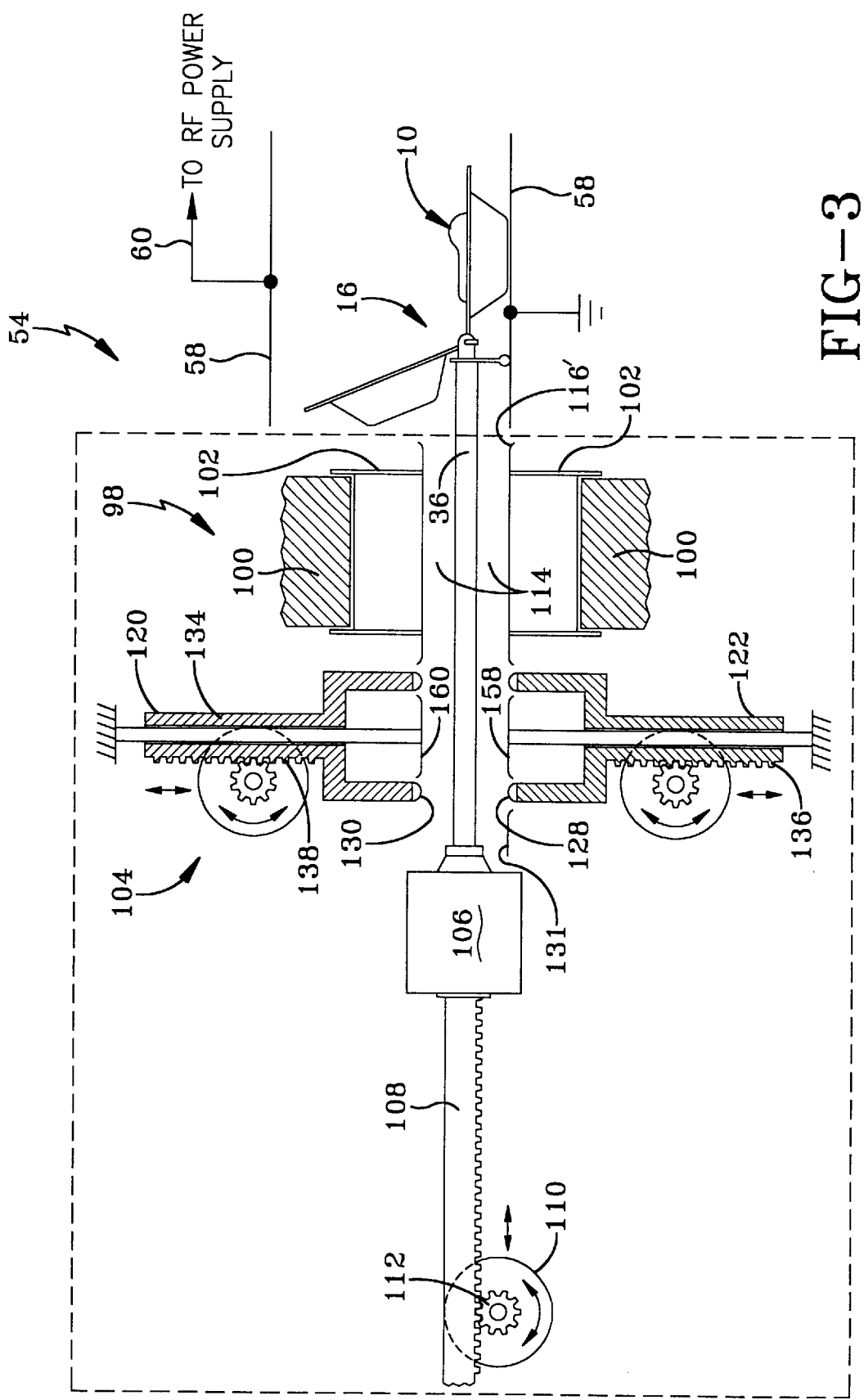

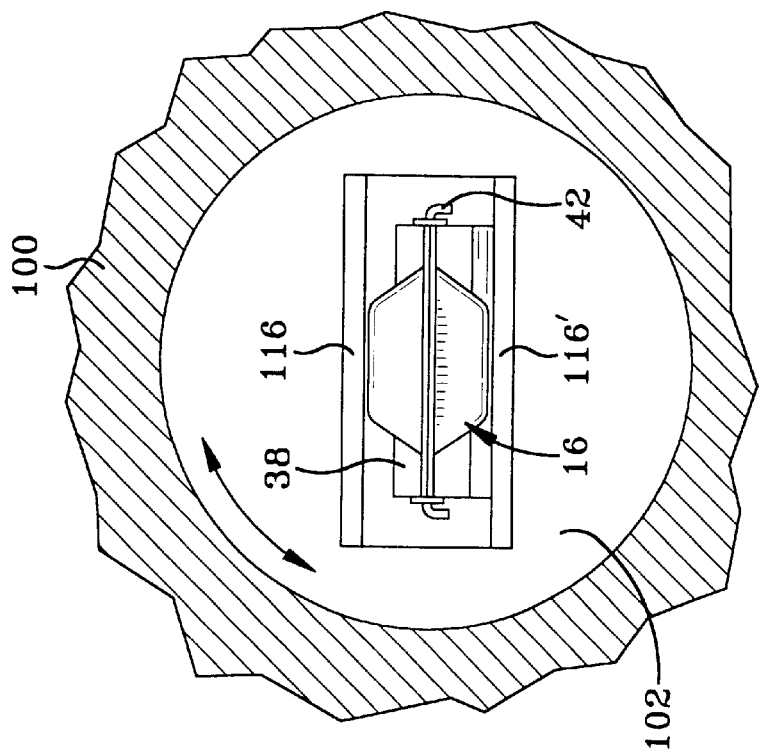
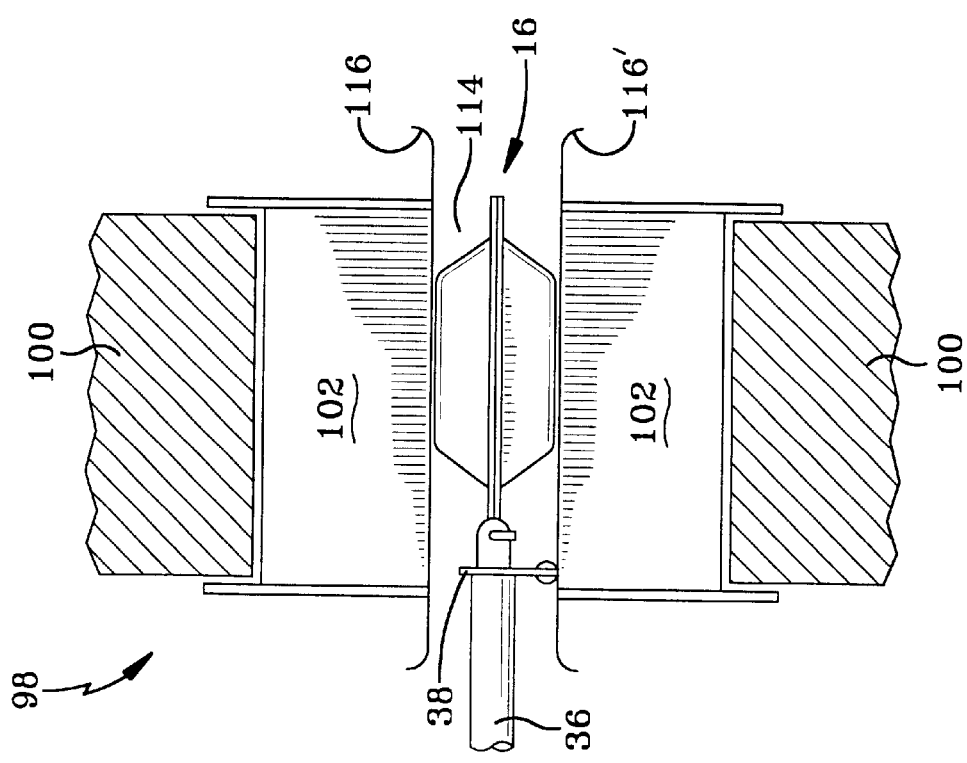
FIG-4B
FIG-4A

REMOVAL OF BIOLOGICALLY ACTIVE ORGANIC CONTAMINANTS USING ATOMIC OXYGEN The invention described herein was made by an employee of the United States Government and others who have assigned all of their right title and interest in and to the invention which may be manufactured and used by or for the Government for Government purposes without the payment of any royalties thereon or therefor.

BACKGROUND OF THE DISCLOSURE

1. Field of the Invention

The invention relates to an apparatus and method for using atomic oxygen to remove biologically active organic contaminants from the surface of surgical implants and other biomedical devices. More particularly, the invention relates to an apparatus and method for using an atomic oxygen plasma to remove non-living, but biologically active organic contaminants, including endotoxin contaminants, from the surface of surgical implants and other biomedical devices, and the containers used for storing and transporting them, to produce a biologically clean device and container. The process also includes hermetically sealing the device in the container, in-situ in the plasma chamber to form a hermetically sealed package, which may then be gamma ray sterilized for storage and transport.

2. Background of the Invention

It is imperative that surgical implants and other biomedical devices used in or which come into contact with living tissue in a live mammalian or other host body, be free of biologically active organic contaminants, such as endotoxin materials which cause an inflammatory reaction in the host body. The inflammatory reaction can lead to failure of the implant or device to function properly. For example, with surgical implants such as artificial hip joints, heart valves and the like, despite substantial research efforts there is still at the present time a significant failure rate of implants in the human body. This can be due to the inflammation of the surrounding living tissue which grows onto and adheres to all or part of the surface of the device. Inflammation is believed to be due to the presence of endotoxins or other biologically active surface contaminants that are difficult to remove. Various plasmas and chemical treatments have been reported for sterilization, but not for endotoxin removal. Examples of some of the plasma treatments disclosed for sterilization may be found in, for example, U.S. Pat. Nos. 3,948,601; 5,656,238; 5,482,684; 5,163,458 and 5,087,418. Methods for removal of such endotoxins invariably relate to chemical cleaning methods. Even if such a device is successively sterilized, certain endotoxins such as cellular material comprising lipopolysaccharides are typically not removed from the surface of the device. Endotoxins consisting of cellular material, and particularly lipopolysaccharides, have been found to be inflammatory and resistant to removal even after multiple, sequential alcohol/alkali baths followed by acid baths, followed by washing and rinsing. Such multiple baths at elevated temperatures on the order of at least 220° C. for four or more hours are the only known methods which have successively removed cellular endotoxins. While high temperatures on the order of about 400° C. may thermally decompose biologically active organic contaminants, including endotoxins, such high temperatures may impair the fatigue life of metal implants and will destroy most plastic implants, such as an acetabular cup used in hip implants. Multiple acid and alkali baths degrade polymeric materials, as well as some metal implant materials, and temperatures over about 100° C. will damage many polymeric materials. Further, such methods have not been proven to remove all biologically active contaminants from the surface of implants. Therefore, it would be an improvement to the art if endotoxins, including cellular material comprising lipopolysaccharides, could be removed from the surface of both a biomedical device and a container for storing and transporting the device prior to use, without having to resort to harsh, and materials damaging, chemical and heat treatments.

SUMMARY OF THE INVENTION

The invention relates to a low pressure and temperature process which comprises (a) using an atomic oxygen plasma to remove non-living, but biologically active organic contaminants, including endotoxins, from the surface of (i) surgical implants and other biomedical devices, and (ii) containers for storing and transporting them, to produce bioclean devices and containers, and (b) hermetically sealing the device in the container, and to an apparatus useful in the process. Hermetically sealing the device in the container produces a package containing a bioclean device, which may then be sterilized in-situ in the sealed container with gamma radiation. The plasma is generated in a hermetically sealed plasma chamber. By bioclean in the context of the invention is meant that those surfaces of a biomedical device which will come into contact with living tissue in a host body or elsewhere (hereinafter "biosurfaces") and those surfaces of its container which will come into contact with such biosurfaces during the cleaning and sealing (hereinafter "contact surfaces"), are free of biologically active organic contaminants comprising endotoxins, such as cellular material and lipopolysaccharides, as a result of being processed according to the practice of the invention. Thus, the process of the invention biologically cleans both those surfaces of the biomedical device that will come into contact with living tissue in a host body or elsewhere and those surfaces (e.g., the interior surfaces) of the container or package which contact the biosurfaces during the cleaning and sealing. In the process of the invention, the entire surface of an implant, such as a hip implant, is biocleaned by the oxygen plasma. This is achieved by means in the plasma chamber, which manipulates either, or both and preferably both, the device and container during the biocleaning. Thus, both the biosurfaces of the device and the contact surfaces of the container are simultaneously biocleaned in the same plasma chamber. Exposing the sealed package to gamma radiation sufficient to sterilize the biosurfaces of the bioclean device, also sterilizes the interior contact surfaces of the sealed container. After the biocleaning, the device is preferably hermetically sealed in its container in the same chamber in which the biocleaning was conducted, a portion of which comprises the plasma space containing the plasma that achieves the biocleaning, and another portion of which contains means for the manipulation and sealing. In a further embodiment, during biocleaning of the device and container, the atomic oxygen generated by the plasma flows through the chamber and also biocleans the interior of the chamber and at least those surfaces of the manipulation and sealing means located in the chamber, that come into contact with both the biosurfaces and contact surfaces during the process. In a still further embodiment, which is a preferred embodiment, at least one precalibrated witness indicator or coupon is placed in the plasma during the biocleaning of the device and container, to provide preferably a readily discernable visual indication, of whether or not the device and container have been in contact with the atomic oxygen for a time sufficient to achieve the desired biocleaning. This is explained in detail below. By low pressure is meant less than about 500 millitorr and preferably from about 0.1 to 300 millitorr, and by low temperature is meant less than 100° C., preferably less than 75° C. and more preferably no greater than 60° C. The process of the invention is in contrast to prior art processes, which usually leave difficult to remove endotoxins, such as lipopolysaccharides and which do not disclose manipulating the device and container during the biocleaning in the sealed atomic oxygen chamber, so that all biosurfaces and contact surfaces are biocleaned prior to sealing.

An apparatus useful in the practice of the invention broadly comprises a hermetically sealable chamber containing (i) means for generating an atomic oxygen plasma in the chamber and (ii) means for manipulating the biomedical device and its container in the chamber. It will also comprise means for introducing oxygen or a gas comprising oxygen through the chamber at a controlled flow rate, means for evacuating the chamber to the desired subatmospheric pressure and means for inserting and removing the device and container from the chamber. The chamber will preferably also contain means for inserting the biocleaned device into the biocleaned container means, means for closing the container over the device prior to sealing and means for sealing the closed container containing the device, following the atomic oxygen cleaning. The means for generating the atomic oxygen plasma may simply be a pair of opposing and spaced-apart flat plates which comprise a pair of electrodes electrically connected to a suitable high voltage source, with the space between the electrodes defining the region in which the plasma exists, and in which cleaning of the device and container is achieved. A high voltage radio frequency (RF) source, which provides a high voltage RF to the electrodes, is typically located outside the chamber.

Thus, in a broad sense and in one embodiment, the invention relates to a process for biocleaning (i) the biosurfaces of a biomedical device and (ii) at least the contact surfaces of an open, but closeable and hermetically sealable container means for the device, wherein both said biosurfaces and contact surfaces are contacted with atomic oxygen at low temperature and subatmospheric pressure, in a hermetically sealed chamber, and wherein said atomic oxygen is produced by a plasma. In a more specific sense the process comprises biocleaning (i) the biosurfaces of a biomedical device containing non-living, biologically active organic material, including endotoxins and (ii) at least the contact surfaces of an open, but closeable and hermetically sealable container means for the device, with atomic oxygen at low pressure and temperature in a hermetically sealed chamber, for a time sufficient to remove the biologically active organic material, including endotoxins, from these surfaces by oxidation, followed by closing the biocleaned container means over the biocleaned device and then hermetically sealing the container means in the chamber, wherein the device is manipulated during the biocleaning, to insure that all of the biosurfaces and contact surfaces have been biocleaned. This thus forms a hermetically sealed package containing a bioclean device enclosed within, in which the contact surfaces of the container are themselves bioclean. The hermetically sealed package is then preferably exposed to gamma radiation to sterilize the bioclean biosurfaces of the device and the bioclean container contact surfaces inside the container. The device remains bioclean and sterile inside the container. The container means is fabricated of material that is not permeable to biologically active material and will typically comprise a polymeric material which can be sealed to itself by heat, ultrasonics or adhesive means. In a preferred embodiment the container means is fabricated, in clamshell fashion, as a unitary body comprising two halves joined together at a common hinge means which, after the biocleaning is achieved, are hermetically sealed to each other to form a package containing the biocleaned device, and preferably also the witness coupon. A container means fabricated of a resilient thermoplastic has been found to be useful in this embodiment.

BRIEF DESCRIPTION OF THE DRAWINGS

FIG. 3 is a partial schematic side view of a means for manipulating and sealing the implant and container used in the apparatus of FIG. 2.

FIGS. 4(a) and 4(b) are schematic side and end views of means for closing and rotating container containing the implant the vacuum chamber.

DETAILED DESCRIPTION

Figure 1:
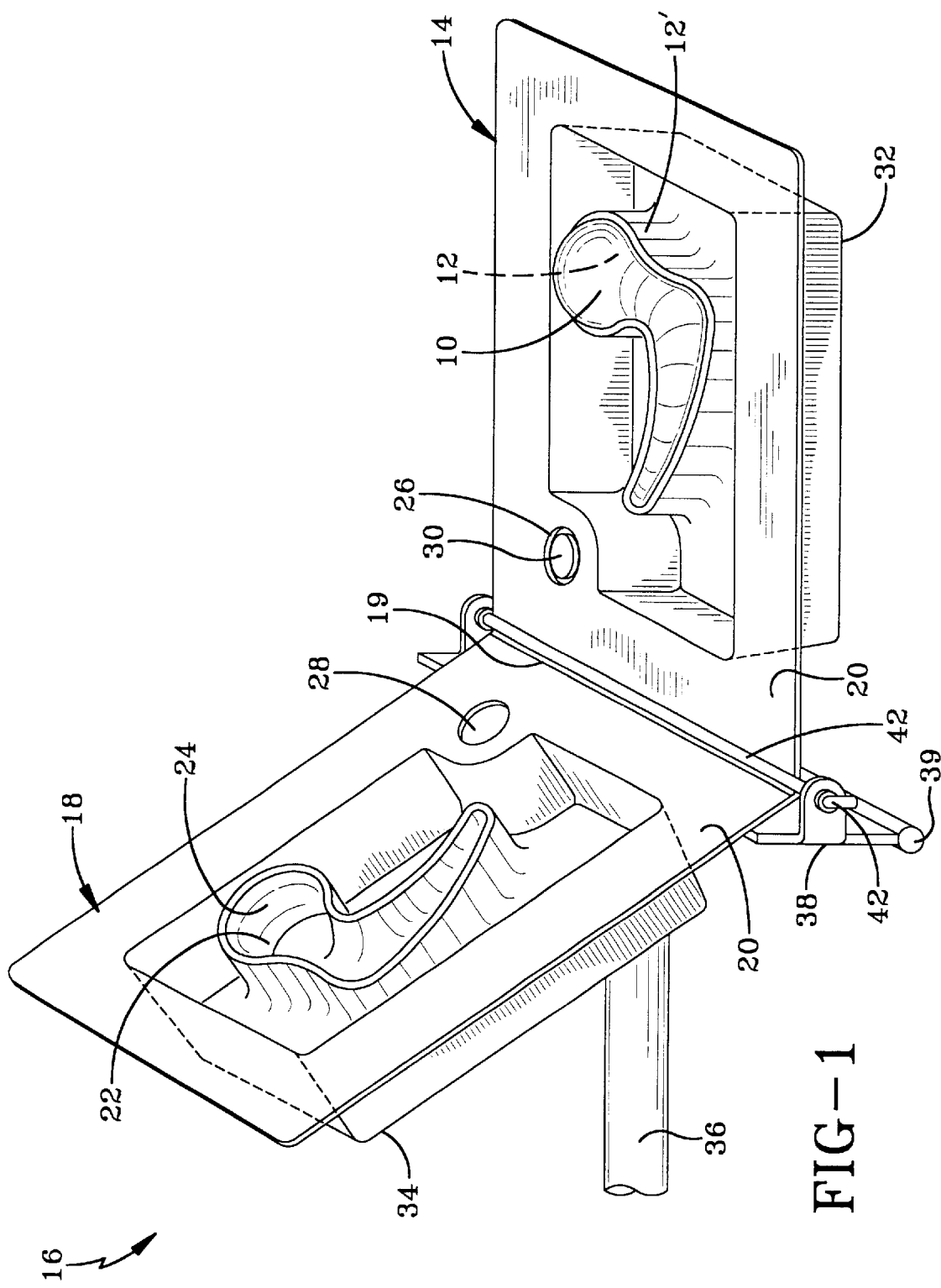
FIG. 1 is a schematic side view, in partial perspective, of an artificial hip joint implant supported in half of a heat sealable, open container fabricated in clamshell fashion.

As mentioned above, the process of the invention is in contrast to prior art processes which use an inert gas or oxygen plasma for sterilization, but are not effective for removing endotoxins, such as lipopolysaccharides, and which do not disclose manipulating the device and its container in the atomic oxygen, so that all biosurfaces of the device and contact surfaces of the container means are biocleaned prior to sealing. It has been found that removal of certain endotoxins, particularly lipopolysaccharides, is more difficult to achieve than mere sterilization. Thus, the biosurfaces of a biomedical device sterilized by prior art methods may be sterile, yet still contain biologically active, non-living organic material which comprises one or more endotoxins. Lipopolysaccharides for example, are endotoxins that are present in mammalian cellular material and in cellular material from other life forms, and are transferred to the device by simple contact with living tissue, through handling occurring during manufacturing, inspection, storage and transfer, packaging, etc. For example, mammalian cellular material, including lipopolysaccharides, is found in fingerprints. As a practical matter it is extremely difficult and sometimes almost impossible to avoid endotoxin contamination. This is why the present invention, which biocleans the biosurfaces of the biodevice and contact surfaces of the container, followed by packaging the bioclean device in the bioclean container, which is then hermetically sealed under endotoxin free conditions, produces a device that remains bioclean and which can then be gamma radiation sterilized without opening the container. Thus, the device remains bioclean and sterile in the container. When the container is opened and the device removed, the use of bioclean instruments and surgical gloves for removing the device and placing it in a host body or into contact with mammalian or other living tissue for use, prevents or at least greatly reduces the chances of recontamination, so that the bioclean device remains so. With respect to artificial implants for humans and animals, this will greatly reduce the chances of inflammation and inflammatory response, which often leads to failure of the device or its ability to function properly.

In the process of the invention, a medical device such as a surgical implant to be surface cleaned of non-living, biologically active endotoxin organic contaminants such as or including lipopolysaccharides present on its biosurfaces, is placed in a hermetically sealed vacuum chamber, either on a support means on which it rests or held in the atomic oxygen plasma by grasping means. The biosurfaces of the device that are not supported or held are therefore exposed to, and contacted by, the plasma. After the exposed biosurfaces of the device have been contacted by the atomic oxygen plasma for a time predetermined to be sufficient to remove the contaminants, the device is manipulated in the chamber by biocleaned means, so that all or a portion of the biosurfaces that were biocleaned are now supported on or by means whose contact surfaces are also bioclean. Typically, these contact surfaces are biocleaned in the same plasma in the same chamber and at the same time that the surfaces of the device are being cleaned. The remaining biosurfaces are then biocleaned. Although the contact surfaces of the container means in which the bioclean device is to be sealed may be biocleaned in a separate plasma in the same chamber, or in another chamber which is connected to the chamber in which the device is biocleaned, it is preferred to bioclean the contact surfaces of the container in the same plasma and at the same time that the device is being biocleaned. Still further, the contact surfaces of the container means may comprise the support means for the device in the plasma, as is illustrated in the embodiment shown and described below. Thus, the support means may be permanently in the chamber or it may be suitable surfaces of the container means in which the device is to be sealed, after it has been biocleaned by the atomic oxygen treatment of the invention.

In the embodiment illustrated in the Figures, the medical device to be cleaned is a surgical implant, specifically illustrated as an artificial hip joint, which is initially placed on an interior support surface formed by a cavity in one half of an open and hermetically sealable plastic container means, fabricated in clamshell fashion as a unitary body, having two mating halves joined together at a resilient plastic hinge portion. The plastic is a resilient, hermetically heat sealable thermoplastic. By resilient is meant that it has some stiffness and, when bent, will return to its former position after the bending forces have been removed. This enables the container means to open by itself at the hinge portion, after it has been closed over the device, turned over and removed from the closure and turning means. Less than half of the biosurfaces of the device and less than half of the contact surfaces of the container half are in contact, thereby leaving more than half of both surfaces exposed to the atomic oxygen plasma. The apparatus comprises an atomic oxygen exposure system which includes a hermetically sealed vacuum chamber having means for inserting and withdrawing the device and container means, means for generating atomic oxygen in the chamber, and means for manipulating the device and container in the chamber before and after sealing. The process comprises placing the open container into the open chamber and securing it to a manipulation actuator arm by suitable clamp means. The device is then placed in a support cavity in bottom half of the open container in the chamber. An atomic oxygen witness coupon is also placed in a support cavity provided for it in the bottom half of the container, to provide a record of the extent of the exposure of both sides of the device and container means to the atomic oxygen. This may be a simple thin, orthogonal or coin-shaped coupon fabricated of glass or ceramic, coated on both sides with a layer of carbon of known thickness. Each of the two sides of the witness indicator coupon is exposed to same the atomic oxygen plasma treatment as the corresponding sides of the device and inner container surfaces. In an embodiment in which the coupon is a white ceramic chip, the change in reflectance produced by the carbon removal by oxidation from the atomic oxygen exposure, can be calibrated to be a direct measure of the extent and amount of exposure. The vacuum chamber is hermetically sealed and evacuated by any of a variety of vacuum pumps, to a subatmospheric low pressure in the chamber in the range of from about 1 to 300 millitorr. An atomic oxygen plasma is formed in the chamber and both the biosurfaces and the contact surfaces are exposed to the atomic oxygen, under conditions and for a time sufficient to remove non-living, biologically active organic material, including endotoxins, from the exposed surfaces by oxidation. The top cover of the container is then closed by the moving the container into contact with a closing and turning means in the chamber, by means of the actuator arm and clamp. The closed container, which contains both the partially biocleaned device and witness coupon, is then turned upside down and removed from the closing and turning means by the actuating arm and clamp means. A hinge means comprising the portion of the unitary clamshell container means at the midpoint between the mating halves, combined with the use of a resilient thermoplastic, results in the former bottom half, which is now the top half, of the container means to open. The device (and the witness coupon) are now supported in respective cavities in the former top half, which is now the bottom half of the container means. Thus, those surfaces which were not exposed to the atomic oxygen plasma, are now exposed to it by means of the manipulation. The atomic oxygen plasma is maintained and continued to bioclean all previously uncleaned surfaces. The container is then closed over the bioclean device and bioclean container surfaces and the witness coupon, in the same manner as before. The closed container is manipulated into a heat sealing means in the sealed chamber, and heat sealed by pressing and softening the plastic to adhere to itself around a flange means laterally extending from each half, to produce a hermetically sealed package containing the bioclean device. The sealed package is then exposed to gamma radiation to sterilize the implant in its sealed container. The package is then stored or transported, etc. and the biomedical device in it remains sterile and free of endotoxins, for as long as the package remains sealed. The color or reflectance of the witness coupon seen on opening the sealed container, indicates whether or not the device has received the proper amount of contact with the atomic oxygen plasma. In another embodiment, which is a preferred embodiment, that portion of the thermoplastic container formed into the mating recesses that support the witness during the treatment, will be fabricated of light transparent plastic, so that it can be seen before opening the hermetically sealed container, whether or not the device has received the proper amount of contact and exposure to the atomic oxygen plasma. Thus, the surfaces of the device in the sealed container that will come into contact with living tissue when used, are bioclean and sterile. The container is made of a plastic material that is impervious to penetration of non-living biologically active organic material and also living organisms, such as bacteria and viruses.

Referring to FIG. 1, a metal artificial hip joint implant 10 is shown supported in a cavity 12 formed in the bottom half 14 of a heat sealable, resilient thermoplastic open container means 16. Container means 16 is a unitary body, fabricated in clamshell fashion with its top 18 and bottom 14 halves merging together at hinge portion 10, which is merely a fold or crease in the contiguous sealing flange 20 common to both halves. In the embodiment shown, a cavity 22 in the top half 18 of the container means, provides support for the implant when the container means has been turned over after the first phase of the atomic oxygen plasma biocleaning, as is explained below. The cavity 12 in which the implant 10 reposes is similar to cavity 22, but is not clearly shown due to the presence of implant 10 supported by, and resting partly therein. Opposite and opposing cavities 26 and 28 provide means for supporting the atomic oxygen treatment indicator coupon 30 which, like implant 10, has its top and bottom exposed to the atomic oxygen treatment at the same time that the corresponding top and bottom portions of the implant are being treated. Thus, the top and bottom portions of the witness coupon receive the same amount of atomic oxygen treatment that the top and bottom portions of the implant do. In this illustration, the witness coupon 30 comprises a thin disk fabricated of white ceramic, having a layer of carbon of a predetermined thickness on its top and bottom surfaces. Coupon 30 is illustrated in detail in FIG. 6 and explained in more detail below. Having at least those portions of the sealing flange that support and contain the coupon fabricated of clear plastic, enables facile visual inspection and determination of whether or not all the biosurfaces surfaces of the implant (and the corresponding contact surfaces of the container) have received treatment adequate enough to insure that all of the biologically active, non-living organic material has been removed. The bottom 32 and top 34 of the corresponding bottom 14 and top 18 halves of container are flat as shown, to enable level positioning in the chamber. In this illustration, cavities 12 and 22 are formed by corresponding molded sidewall portions 12' and 24, which protrude up from the otherwise flat and level corresponding bottoms 32 and 34. Part of the means for manipulating the implant and container is briefly shown in part in FIG. 1 as including an actuator arm 36 capable or rotating about its longitudinal axis, as well as transverse motion in both directions along its longitudinal axis. A clamp or holding means 38 is attached to one end of 36. A rod 39 extends across the bottom of 38, to insure that the implant container means, and the implant containing container after closure and sealing, is guided smoothly over the surface of the bottom atomic oxygen plasma electrode 58 (see FIG. 2), and a removable pin 42 supported by the holding means 38, extends across the hinge portion 19 of the two halves. Operation of the manipulating means to close, rotate, open and close again, and heat seal the implant and container assembly is shown in FIGS. 2–5 and described below.

Figure 2:
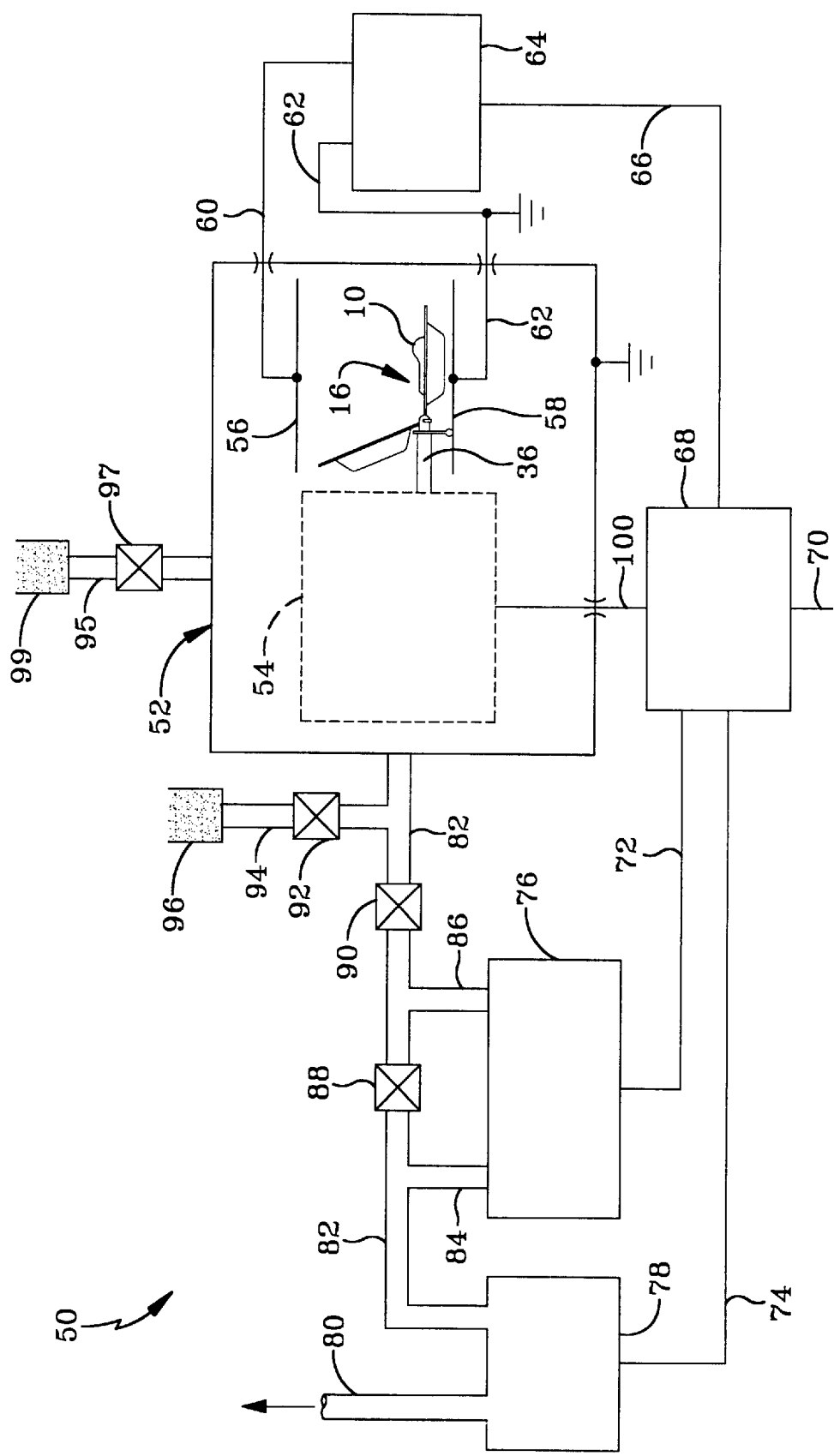
FIG. 2 is a brief schematic side view of an apparatus useful in the practice of the invention.

Turning to FIG. 2, the apparatus useful in the practice of the invention is briefly shown in schematic side view. Thus, apparatus 50 is shown as comprising a hermetically sealed vacuum plasma chamber 52 containing within a means 54, shown by the dotted lines and described in detail in FIGS. 3–5, for manipulating the implant 10 and container means 16 and then sealing the implant in the closed container. The implant 10 is shown disposed in the cavity 12 (not shown) in the bottom half of the open container, which is held between two opposing electrodes 56 and 58, by means of the manipulating device partially shown and including actuator arm 36. Electrodes 56 and 58 are electrically connected to an RF power supply 64 operated at a frequency of typically 13.56 MHz, which is the frequency presently permitted for generating atomic oxygen plasmas. A power level appropriate for the vacuum chamber size is used to produce an acceptable atomic oxygen Kapton effective flux (e.g., typically>$1 \times 10^{15}$ atoms/cm$^2$ sec). RF power is introduced into the vacuum chamber by power cables 60 and 62, with 62 also connected to a ground, as shown. Power cable 66 electrically connects the RF power supply 64 to the power and electronics control module 68 which, in turn, receives its power from electric power input cable 70. The atomic oxygen plasma may be generated by an RF, direct current or microwave plasma generating system although RF is preferred because of its simplicity. Power supply 70 also provides electrical power to blower and vacuum pumps 76 and 78, by respective electrical power cables 72 and 74. The blower and vacuum pumps, as well as a repressurrization ultra filter 96, are all interconnected to each other and to chamber 52, via gas conduits 82, 84, 86 and 95. Valves 88, 90 and 92 permit any three or all of these units to be isolated from the vacuum chamber 52 and from any one or two of the others. Gas conduit 80 serves as an exhaust port to the ambient for the vacuum pump 78. Electrical cable 100 electrically connects the power and control module 68 to the manipulating and sealing means 54. A mixture of oxygen and inert gas, such as oxygen and argon or air, and preferably air, is introduced into the chamber by means of gas conduit 95, containing an inlet gas flow control valve 97 and an ultrafilter 99, which prevents bioactive dust particles from entering the vacuum chamber. Not shown is a hermetically sealable means or chamber door for inserting the implant and container into the chamber and then removing the biocleaned implant-sealed container assembly or package. FIG. 3 is a side view schematic of the manipulating and sealing means 54, which manipulates the implant 10 and container 16, and then seals the implant in the closed container. Referring now to FIG. 3, manipulating and sealing means 54 is shown as comprising a rotating means 98, a heat sealing means 104 for hermetically sealing implant 10 in a container 16, a reversible rotary motor means 106, an axial motion, reciprocating rack gear activator rod 108 and a reversible motor 110, having a gear 112 attached to the motor, in meshed relationship with the teeth in rack gear 108. Means 98 is shown in detail in FIGS. 4(a) and 4(b) as comprising a fixed housing 100 having a rotatable sleeve 102 within, for closing the container 16 over the implant 10 within, and then rotating the implant 10 and container 16 assembly inside chamber 114. Motor 110 is able to rotate in two directions about is axis of rotation, so that, by means of gear 112, bar 108 (see FIG. 3) is able to move in both directions along its longitudinal axis. One end of bar 108 is also attached to motor 106, to provide axial motion to that motor and to actuator arm 36, which is attached at one end to motor 106 and at the other end to container means 16. In operation, once the first exposed outer surfaces of implant 10 and the exposed inner surfaces of container means 16 have been exposed to the atomic oxygen for a time previously determined to be sufficient to bioclean and thereby remove all non-living biologically active organic material, including lipolysaccharides and other endotoxins, motor 110 is actuated to rotate gear 112 counterclockwise. This pulls, via the combination of axial activator bar 108, rotary motor 106 and actuator arm 36, container means 16 containing implant 10 back into the interior cavity 114 of rotatable sleeve 102, as shown in FIGS. 2, 3 and 4. Longitudinal, curved closure members 116 and 116', located proximate to the top and bottom of the entrance to the cavity 114, and horizontally extending across the entrance thereto, are convexly curved outward to urge the two halves of container means 16 together, as it is pulled into cavity 114 by actuator arm 36. Once the closed container containing the implant is inside the cavity in the rotatable sleeve, motor 106 is actuated and rotates 180°, to turn the container therein upside down, thereby reversing the vertical position of the top and bottom halves of the container means, and the implant and atomic oxygen witness coupon inside. Motor 110 is then rotated in a clockwise direction to push the closed container back out of the sleeve 102 and position it between the two electrodes again. As the closed container leaves the cavity in the sleeve, the top half, which was formerly the bottom half, opens due to the resiliency of the thermoplastic hinge portion of the container means, to re-expose and particularly to expose, its interior surfaces and especially the contact surfaces on which the implant was resting during the first atomic oxygen treatment. The implant is now supported by the cavity in the bottom half of the container means, which was initially the top half. A portion of the biosurfaces of the implant and the contact surfaces of the former top container half 18, which were biocleaned during the first phase of the atomic oxygen treatment, are now in contact with each other, as these biocleaned container contact surfaces now support the corresponding biocleaned implant biosurfaces. Similarly, the biosurfaces of the implant and contact surfaces of the container means half 14, which supported the implant during the first phase of the atomic oxygen biocleaning treatment and were therefore not previously treated, are now exposed to the atomic oxygen plasma to remove nonliving and biologically active organic material remaining on these surfaces. After this, the implant and container means assembly is pulled back into the cavity in the rotatable sleeve, to close both halves and form a bioclean, but unsealed container containing a bioclean implant. Generation of the atomic oxygen is then stopped, the chamber pressurized to atmospheric pressure with air or any suitable inert gas, via at least one repressurization ultra filter 96, valve 92 and conduits 94 and 82. The container is then sealed with the heat sealing means 104. Filter 96 prevents endotoxins and other biologically active contaminants from recontaminating the clean implant and interior container surfaces.

Figure 5:
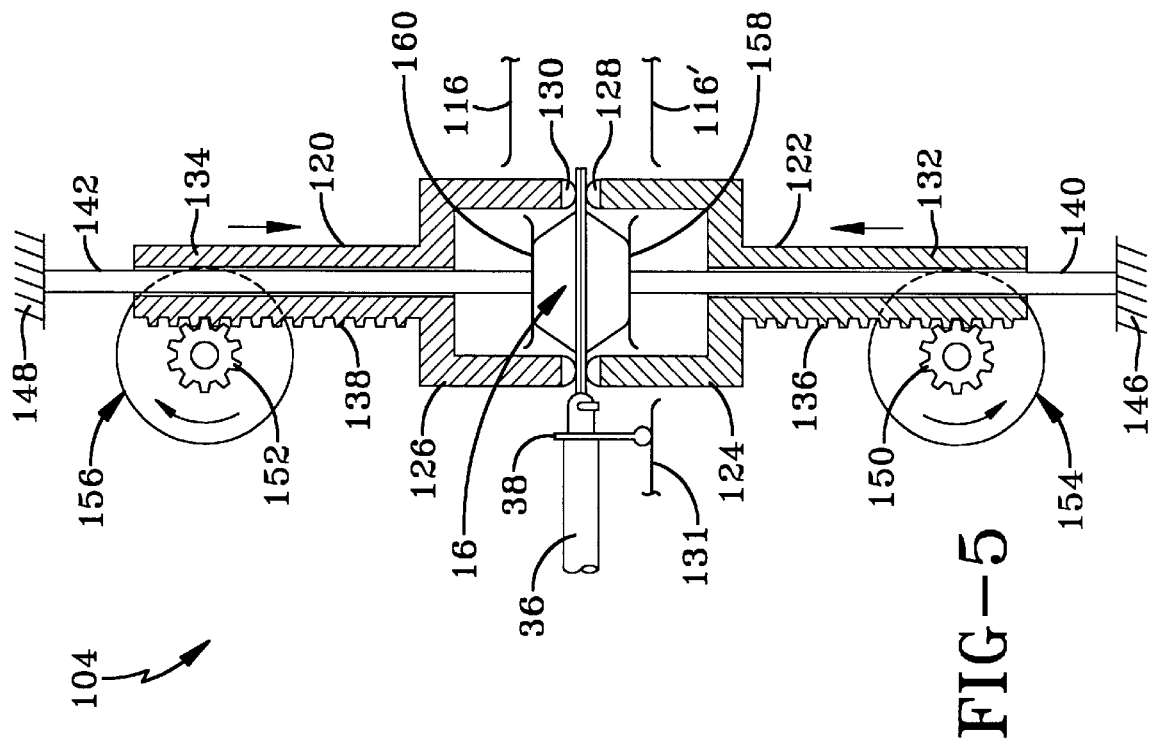
FIG. 5 is a partial schematic side view of a heat sealing means used in an apparatus of the invention.

Referring to FIGS. 3 and 5, sealing means 104 is schematically shown in partial cross-sectional side view and comprises a pair of substantially identical, diametrically opposite and opposing, vertically movable and oriented heat seal clamp means 120 and 122, radially disposed from the longitudinal axis of actuator arm 36. A horizontally disposed flat plate 131 is shown in FIGS. 3 and 5 located just outside of the sealing means 104, with a downwardly curved end proximate 124. This bottom of clamp means 38 rides and rests on the upper surface of 131 as shown, to insure that the closed container means is horizontally level and thereby disposed in the proper position for sealing. Each heat seal clamp means comprises a cup shaped portion at its radially inward end, opening radially inward towards arm 36 and terminating at that end in identically shaped heat sealing means 128 and 130. Means 128 and 130 in this embodiment are hollow metal, each terminating in a smooth arcuately shaped sealing surface containing within means (not shown), such as electrical resistance wires, for heat sealing the rounded sealing surfaces that contact the upper and lower flange portions of the closed container. The shape of the cup and heat sealing means is rectangular and the means is sized to match the shape and dimensions of the desired seal for the closed container. The partially closed end of each cup portion extends radially out in a respective hollow sleeve portion 132 and 134, toothed along one side parallel to its vertical axis and shown as 136 and 138. The hollow interior of each sleeve slides over a corresponding guide rod 140 and 142, each of which is attached to a surrounding frame, of which only a brief portion 146 and 148 is indicated in the drawing. The toothed side of each sleeve is in mating engagement with the teeth in corresponding gears 150 and 152 attached to respective electric motors 154 and 156. The two motors are actuated to move the seal means up and down in opposing fashion, to clamp and then heat seal the container peripherally around its outer flanged portion and then retract the means to release the hermetically sealed container containing the implant. Flat plates 158 and 160 are separated by a distance sufficient to secure the closed container as it is being sealed. In this embodiment, the flanged portion of the closed container extends slightly beyond the outer periphery of the sealing means, and the actuator arm 36, clamp 38 and pin 42, are also outside the outer periphery of the seal means. Following the sealing, the sealing clamps are withdrawn radially outward, the activator arm moved to position the sealed container away from the sealing means and rotatable sleeve, and the chamber is opened. The sealed container is removed from the chamber and pin 42 is removed from the outer, unsealed portion of the container flange. The sealed container is then exposed to gamma radiation to sterilize the implant and interior of the container, prior to handling, warehousing, transportation and storage. Another open container supporting an implant on the bottom half is pinned to the clamp means 38 by pin 42. The chamber is hermetically sealed, depressurized and the atomic oxygen treatment cycle repeated. While in this embodiment, the container assembly is shown as a generally clamshell shaped, unitary body with a resilient hinge portion joining the two opposing halves, those skilled in the art will appreciate that other forms may be used, if necessary or desired. Thus, a separate top and bottom half joined together by a suitable hinge means may be used . Also, an adhesive material may be used to hermetically seal the two halves together, etc. However, the embodiment described above is a preferred embodiment.

Figure 6A:
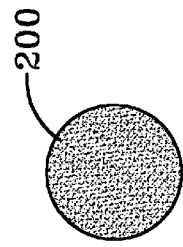
FIGS. 6(a), 6(b) and 6(c) are respective plan, edge and a partial schematic side view in enlarged form, of a treatment coupon useful in the process of the invention.
Figure 6B:
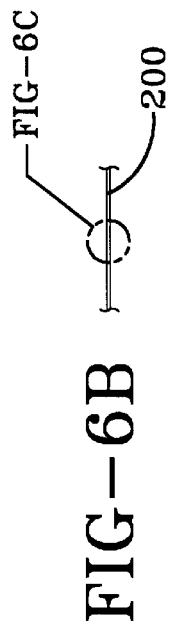
Figure 6C:
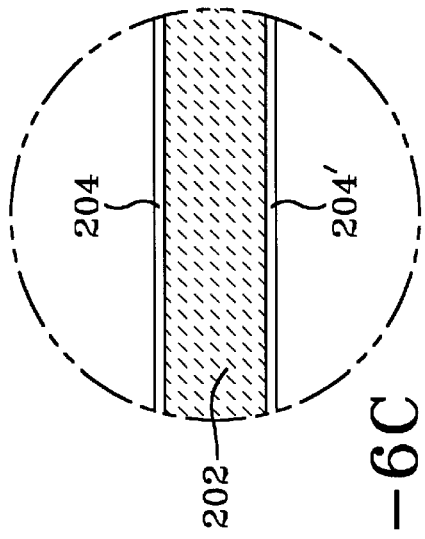

FIGS. 6(*a*), 6(*b*) and 6(*c*) are respective plan, edge and a partial schematic side views in enlarged form, of a coin-shaped atomic oxygen witness coupon 200, useful in the process of the invention. The coupon is shown in FIG. 6(*c*) as comprising a disk 202, coated on both sides with a thin layer of a predetermined thickness of carbon or other substance which will, when removed by the atomic oxygen treatment, provide a contrasting color substrate which indicates that the biomedical device or devices and the interior of the container have received sufficient treatment by the atomic oxygen. The disk 202 may be clear, white or any desired color It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A process for biocleaning (i) the biosurfaces of a biomedical device and (ii) at least the contact surface of an open, but closable and hermetically sealable container means for the device comprising:
   a) Providing a biomedical device and a container for holding the biomedical device;
   b) Providing a hermetically sealable chamber containing means for generating atomic oxygen at low temperature and subatmospheric pressure;
   c) Placing the biomedical device in the container for holding the biomedical device;
   d) Placing the biomedical device contained in the container into the hermetically sealable chamber,
   e) Sealing the chamber;
   f) Generating atomic oxygen at low temperature and subatmospheric pressure and produced by plasma;
   g) Manipulating said container containing the biomedical device in sealed chamber during the generation of atomic oxygen by turning the container containing the biomedical device over at least once to insure that all the biosurfaces are biocleaned by contact with said atomic oxygen.

2. A process according to claim 1 wherein, after said biocleaning and while said chamber is still hermetically sealed, said biocleaned device is hermetically sealed in said container means in said sealed chamber, to form a hermetically sealed container containing said bioclean device within.

3. A process according to claim 2 wherein an atomic oxygen witness means is present in said chamber during said biocleaning.

4. A process according to claim 3 wherein said device is supported on a first contact surface of said container means during part of said biocleaning.

5. A process according to claim 4 wherein, during said biocleaning, said device and container means are manipulated in said sealed chamber so that a biocleaned surface of said device is supported on a second and biocleaned contact surface of said container and said biocleaning in said atomic oxygen plasma is continued until those biosurfaces and contact surfaces which were not biocleaned while said device was supported on said first contact surface, are biocleaned prior to closing and hermetically sealing said container means over said completely biocleaned device.

6. A process according to claim 4 wherein said chamber is opened and said hermetically sealed container is removed.

7. A process according to claim 6 wherein said container means is fabricated of a heat or ultrasonic sealable thermoplastic impervious to penetration by organic material.

8. A process according to claim 7 wherein said container means is a unitary body formed in clamshell fashion to form two matching halves joined by a resilient hinge means.

9. A process for removing non-living, biologically active organic material including endotoxins from biosurfaces of a biomedical device and a container for biocleaning (i) the biosurfaces of a biomedical device and (ii) at least the contact surfaces of an open, but closable and hermetically sealable container means for the device comprising:
   a) Providing a biomedical device and a container for holding the biomedical device;
   b) Providing a hermetically sealable chamber containing means for generating atomic oxygen at low temperature and subatmospheric pressure;
   c) Placing the biomedical device contained in the container into the hermetically sealable chamber;
   d) Sealing the chamber;
   e) Generating atomic oxygen at low temperature and subatmospheric pressure and produced by plasma;
   f) Contacting the surfaces of the biomedical device and container with atomic oxygen at low pressure and temperature to remove biologically active organic material from biosurfaces;
   g) losing the container means over the biomedical device;
   h) Sealing the container containing the biomedical device in the chamber;
   i) Manipulating said container containing the biomedical device in the sealed chamber during the generation of atomic oxygen by turning the container containing the biomedical device over at least once to insure that all the biosurfaces are biocleaned by contact with said atomic oxygen.

10. A process according to claim 9 wherein said sealed container contains visible means which indicates the extent to which said device and container means have been exposed to said atomic oxygen.

11. A process according to claim 10 wherein said hermetically sealed container is exposed to gamma radiation sufficient to sterilize said bioclean surfaces of said container means and said device within.

12. An apparatus useful for biocleaning the biosurfaces of a biomedical device and contact surfaces of a container means, comprising a hermetically sealable chamber containing (i) means for generating an atomic plasma and (ii) means for manipulating both said biomedical device and container means causing container means in a closed condition to be turned over at least once.

13. An apparatus according to claim 12 wherein said apparatus includes means for introducing a gas comprising oxygen into said chamber.

14. An apparatus according to claim 13 wherein said chamber also contains means for closing said container means over said biomedical device means.

15. An apparatus according to claim 14 wherein said chamber also contains means for hermetically sealing said biomedical device in said container.

16. An apparatus according to claim 15 wherein said chamber includes means for placing said biomedical device and container means into it and removing said sealed container from it.

17. An apparatus according to claim 16, which includes means for producing and maintaining a subatmospheric pressure in said chamber during said biocleaning.

18. An apparatus according to claim 17, which includes means for applying a radio frequency to said means for generating said atomic plasma.

19. An apparatus according to claim 18, which includes means for rotating said biomedical device and container means.

* * * * *